(12) United States Patent
Montague (10) Patent No.: US 6,449,777 B1
(45) Date of Patent: Sep. 17, 2002

(54) CHILD-PROOF EYEWEAR RETAINER STRAP ASSEMBLY

(76) Inventor: Janet Linn Montague, 24 Chalmers St., Apartment B, Charleston, SC (US) 29401

( * ) Notice: Subject to any disclaimer, the term of this patent is extended or adjusted under 35 U.S.C. 154(b) by 7 days.

(21) Appl. No.: 09/829,900

(22) Filed: Apr. 10, 2001

(51) Int. Cl.[7] ................................................... A61F 9/02
(52) U.S. Cl. .............................. 2/452; 351/156; 24/3.3
(58) Field of Search ............................ 2/452, 426, 13; 351/123, 155, 156, 157; 24/3.3

(56) References Cited

U.S. PATENT DOCUMENTS

| | | | |
|---|---|---|---|
| 2,504,524 A | * | 4/1950 | Hayward ........................ 2/445 |
| 2,635,239 A | * | 4/1953 | Bivens ............................ 2/12 |
| 3,874,776 A | * | 4/1975 | Seron ............................. 2/452 |
| 3,931,646 A | * | 1/1976 | Loughner ....................... 2/452 |
| 4,515,449 A | * | 5/1985 | Davidson .................... 351/156 |
| 4,657,364 A | | 4/1987 | Murrell |
| 4,976,531 A | | 12/1990 | Kahaney |
| 4,978,210 A | | 12/1990 | Lundbeck |
| 5,002,381 A | | 3/1991 | Murrell |
| D321,702 S | * | 11/1991 | Jennings .......................... 2/12 |
| 5,201,856 A | | 4/1993 | Edwards |
| 5,406,340 A | | 4/1995 | Hoff |
| D377,038 S | | 12/1996 | Yashiro |
| 5,727,259 A | | 3/1998 | Kawamata |
| 5,732,415 A | | 3/1998 | Boyd |
| 5,799,338 A | | 9/1998 | Huang |
| 5,926,855 A | | 7/1999 | Brodbeck |
| 6,019,468 A | * | 2/2000 | Altemare, Jr. ................. 2/444 |

FOREIGN PATENT DOCUMENTS

FR            2611928        *    9/1988

* cited by examiner

*Primary Examiner*—Rodney M. Lindsey
(74) *Attorney, Agent, or Firm*—Harleston Law Firm LLC; Kathleen M. Harleston (57) ABSTRACT

A child-proof strap assembly for retaining eyewear on a wearer's head includes:

a. a flexible lower strap portion of at least two lower strap sections, each lower strap section having a front end and a rear end;

b. a means of detachably attaching the rear ends of the two lower strap sections to one another;

c. a means of attaching the front ends of the two lower strap sections to opposite temples of the eyewear;

d. a flexible upper strap portion of at least two upper strap sections, each upper strap section having a front end and a rear end, the front and rear ends of each upper strap section being affixed to a lower strap section, the front and rear ends of each upper strap section being affixed to a different lower strap section; and e. a means of adjusting the strap assembly to fit the head of the eyewear wearer.

17 Claims, 7 Drawing Sheets

CHILD-PROOF EYEWEAR RETAINER STRAP ASSEMBLY

BACKGROUND OF THE INVENTION

1. Technical Field

The present device is an adjustable, child-proof retainer strap device for holding a pair of eyeglasses on the head of a child, or an adult who is incompetent or in danger of losing his or her eyeglasses.

2. Background Information

The parents or other caregiver of a small child who is temporarily or permanently ill or disabled is often overtaxed and greatly appreciates any small thing that can alleviate their burden. One such small thing that can be done for autistic or developmentally disabled children, or young children with eye (ophthalmologic) disorders that necessitate the wearing of eyeglasses, is to keep their glasses on. Many such children continually pull off and sometimes break or lose their eyeglasses. On occasion, treatment requires that the child wear glasses with one lens covered by a patch in order to strengthen the muscles in the opposite eye. Patches may be worn, for example, by kids with strabismus (squint), sometimes with amblyopia (blurred vision), esophoria (eye turned inward; cross-eyed), exotropia (eye turned outward), etc. Babies born prematurely, which is open the case with multiple births, are particularly prone to eye problems, and it is especially difficult to keep eyeglasses, with or without patches, on several, active small children at once. Young children understandably resist such treatment, even though it is necessary, and sometimes imperative, for improvement of the eye condition.

At the other end of the age spectrum are many older adults with Parkinson's, or Alzheimer's or age-related senility who also will not or cannot keep their eyeglasses on. Their glasses are often necessary, though, to help them ambulate without hurting themselves, and just to help them to better enjoy life. Also, replacing broken or lost glasses can become expensive and inconvenient.

Various devices exist to retain eyewear securely on a person's head. Some of these are designed to provide a means of holding the glasses while the wearer is exercising or engaged in other physical activity during which the glasses may slip and fall. Others are intended for use with swimming goggles. Typically, these devices are designed for adjustability and ease of attachment and removal. There is nothing currently available, however, for securing glasses or other eyewear on a small child or elderly adult so that the glasses cannot easily be removed.

Thus, there is a need for a retaining, and restraining, device that will secure a pair of eyeglasses on the head of a resisting young child or elderly person and make it difficult for them to remove the glasses themselves. The present invention accomplishes this, along with the advantages of adjustability, comfort, and washability. The invention may also be used for securing eyeglasses on persons of any age who are mentally ill, developmentally disabled, or otherwise in need of a device for retaining their eyeglasses on their face. In general, the present invention is an assembly of straps, buckles, and clasps, which are attached to and hold in place a pair of eyeglasses.

BRIEF SUMMARY OF THE INVENTION

The assembly generally includes a pair of lower strap portions, right and left, which are generally mirror images of each other, and an upper strap portion which joins the two lower strap portions. In the preferred embodiment, each lower strap portion is comprised of straps that are removably attachable to the eyeglass frame at the temple hinge. The lower strap portions extend from the temple hinges around the wearer's head and across the bottom of his or her ear. The two lower strap portions are connected to one another at the base of the head, preferably by means of a clasp. In a preferred embodiment, the upper strap portion comprises a pair of similar straps crossing over the top of the wearer's head in an "X" pattern and running generally from each temple hinge, where they are attached to the lower strap portion, across the top of the head to the bow of the opposite temple, where they are joined to the lower strap portion. Buckles, hook and loop fasteners, or other suitable fasteners in the assembly provide adjustability for a secure and comfortable fit. In the preferred embodiment, the straps are made of a fabric that is both comfortable and washable. As designed and properly worn, the invention provides a secure and comfortable means of retaining eyewear that can be easily removed by the parent, guardian, or caregiver of a child or incompetent person. It also provides a superior means of securing eyewear to any person engaged in strenuous physical activity during which eyeglasses may be dislodged.

In summary, the present child-proof strap assembly for retaining eyewear on a wearer's head includes:

a. a flexible lower strap portion comprised of at least two lower strap sections, each lower strap section having a front end and a rear end;

b. a means of detachably attaching the rear ends of the two lower strap sections to one another;

c. a means of attaching the front ends of the two lower strap sections to opposite temples of the eyewear;

d. a flexible upper strap portion comprised of at least two upper strap sections, each upper strap section having a front end and a rear end, the front and rear ends of each upper strap section being affixed to a lower strap section, the front and rear ends of each upper strap section being affixed to a different lower strap section; and e. a means of adjusting the strap assembly to fit the head of the eyewear wearer.

BRIEF DESCRIPTION OF THE SEVERAL VIEWS OF THE DRAWINGS

A more complete understanding of the invention and its advantages will be apparent from the following detailed description taken in conjunction with the accompanying drawings, wherein examples of the invention are shown, and wherein.

DETAILED DESCRIPTION OF THE INVENTION

In the following description, like reference characters designate like or corresponding parts throughout the several views. Also, in the following description, it is to be understood that such terms as "front," "back," "upper," "lower", and the like are words of convenience and are not to be construed as limiting terms. Referring in more detail to the drawings, the invention will now be described.

Figure 1:
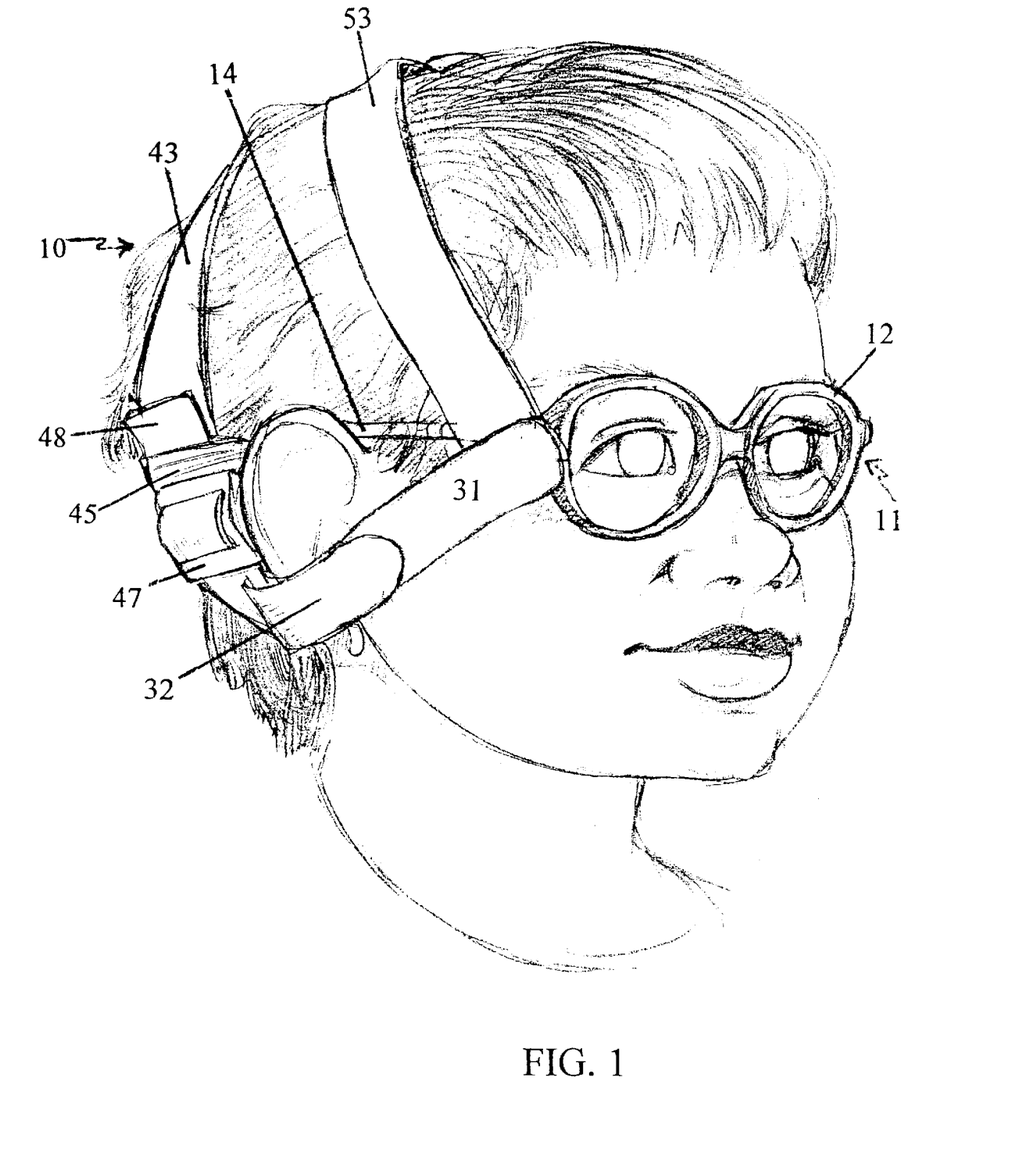
FIG. 1 is a perspective view of a child wearing eyeglasses and a strap assembly according to the present invention.
Figure 2:
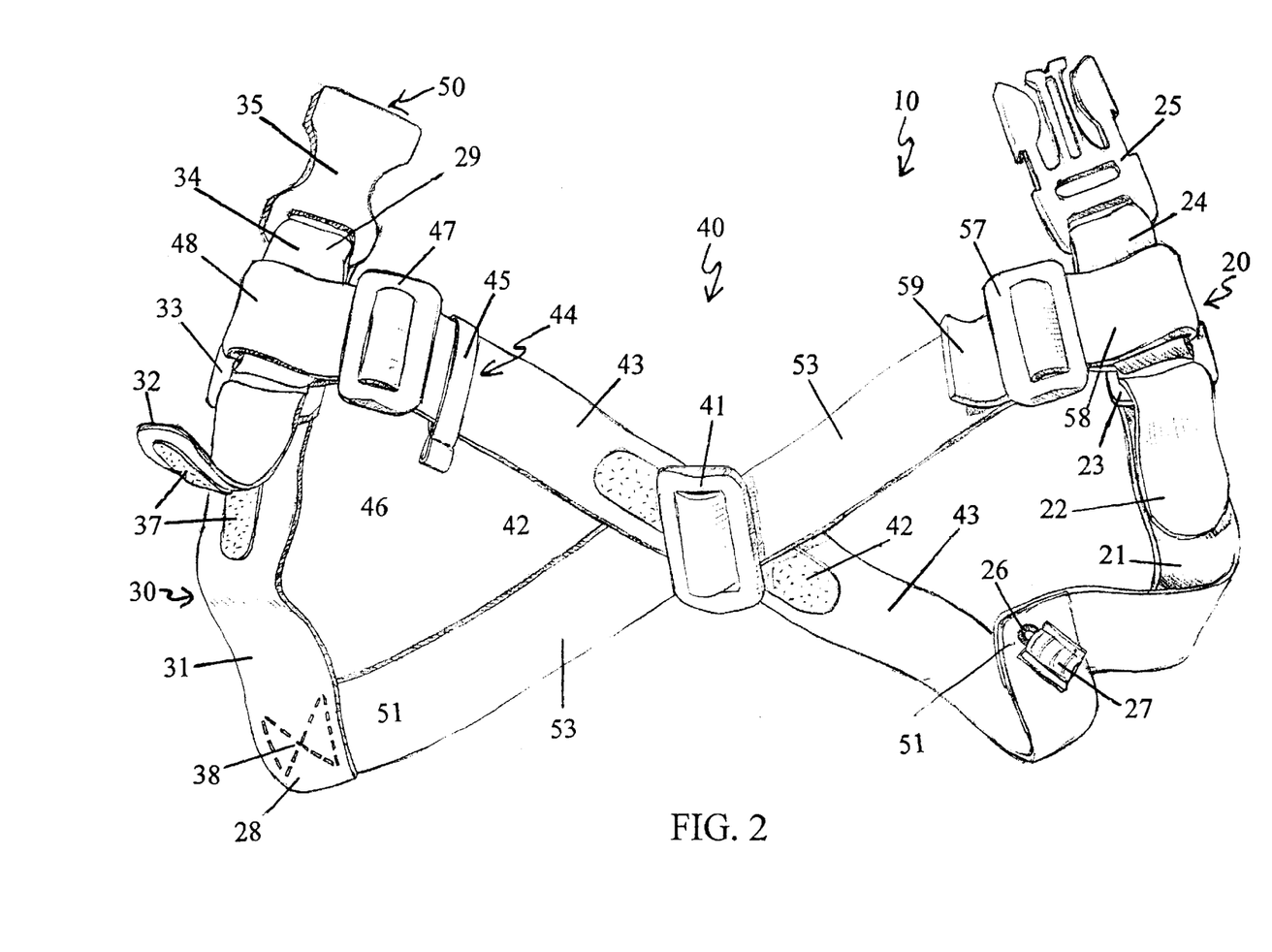
FIG. 2 is a perspective view of a strap assembly according to the present invention.

Referring to FIGS. 1 and 2, a preferred embodiment of an adjustable, child-proof strap assembly, generally referred to as 10, for securing a pair of eyeglasses to the head of a young child or an impaired person is shown. FIG. 1 shows the strap assembly 10 in use on a child's head, and FIG. 2 shows a relatively flattened strap assembly 10. By "child-proof" is meant that it is very difficult for a young child or impaired adult wearer to remove the headgear and the glasses themselves. On the other hand, it is not at all difficult for a caretaker to assemble or remove the strap assembly 10 from the young child's or impaired adult's head. The strap assembly 10 is designed to be removably attached to, and hold in place, a pair of eyeglasses 11 or other similar eyewear.

As shown in FIGS. 1 and 2, the strap assembly 10 generally includes a pair of lower strap sections, right 20 and left 30, which are generally mirror images of each other, and an upper strap portion 40, which joins the two lower strap sections 20, 30. In referring to FIG. 1, the left side of the assembly appears on the left side of the figure and is from the point of view of the viewer; however, the reverse would be true from the vantage point of the wearer. The lower strap sections 20, 30 are so named herein because they fit on either side of the head generally below the wearer's temples, and the upper strap portion 40 is so named because it fits across the head generally above the wearer's temples. Each lower strap section 20, 30 extends from a corner of the eyeglass frame 12 around the head and across or just below the wearer's ear lobe until the right and left lower strap sections 20, 30 fasten to one another at the back of the head at the wearer's hairline, just above the nape of the neck. The fastening mechanism is preferably a squeeze clasp mechanism comprised of male and female complementary clasp portions 25, 35. Any suitable, reusable attachment mechanism may be employed, though. FIG. 2 shows the clasp mechanism with the male clasp portion 25 on the right, and the complementary female clasp portion 35 on the left; however, the clasp portions 25, 35 could be reversed with equal effect.

Figure 3:
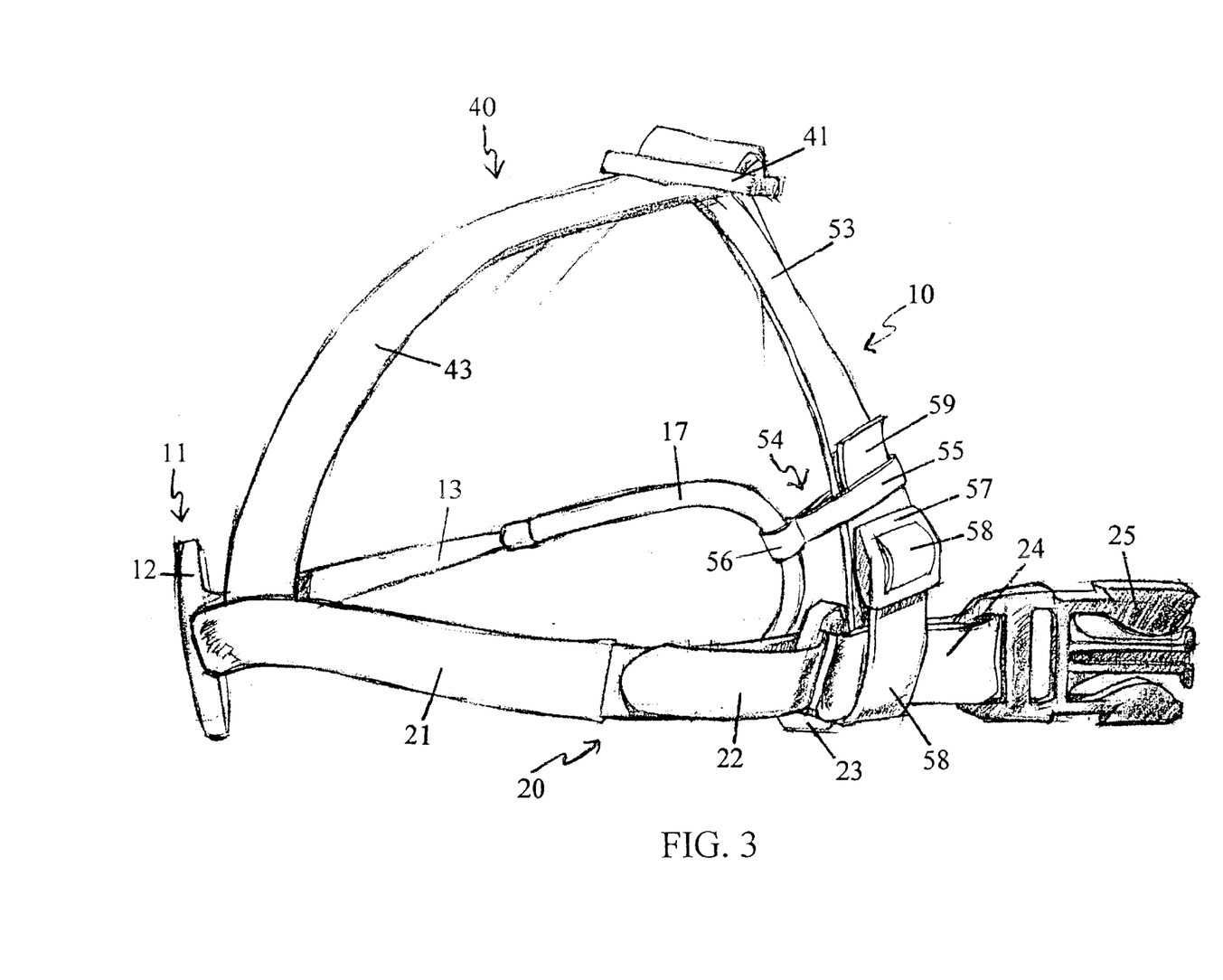
FIG. 3 is a perspective view of a strap assembly according to the present invention, shown attached to a pair of eyeglasses.

Referring to FIGS. 2 and 3, each lower strap section 20, 30 comprises two segments, a front strap segment 21, 31 and a rear strap segment 24, 34. On each side, a reusable attachment mechanism, preferably a buckle 23, 33, connects the front and rear segments. The buckle is permanently attached to the rear segment 24, 34. A flap 22, 32 at the end of the front segment is passed through the buckle 23, 33 and doubled back on itself and fastened by means of a hook and buckle type fastener 36. The flap on the left side 32 is depicted in FIG. 2 partially open to show the hook and buckle fastener 37 beneath. The flap on the right side 22 is depicted in FIG. 2 fully secured and thus the hook and loop fastener is not shown; however, the flaps and fasteners are identical on both sides. The length of each lower strap portion is adjustable by varying the position of the flap 22, 32 with the hook and loop fastener 37, thus allowing the lower strap portion to be tightened or loosened to fit the wearer's head. This provides an important advantage, since each person's head is uniquely shaped, and one side of the head may even be shaped slightly differently from the other side. Also, a single strap assembly can be adjusted as the young wearer grows from month to month, or even week to week. A good fit means that the assembly 10 is more difficult to remove without unfastening the clasp mechanism 25, 35. One half of the squeeze clasp is attached at the end of each rear segment, male 25 to one segment 24, and female 35 to the other segment 34.

Figure 4:
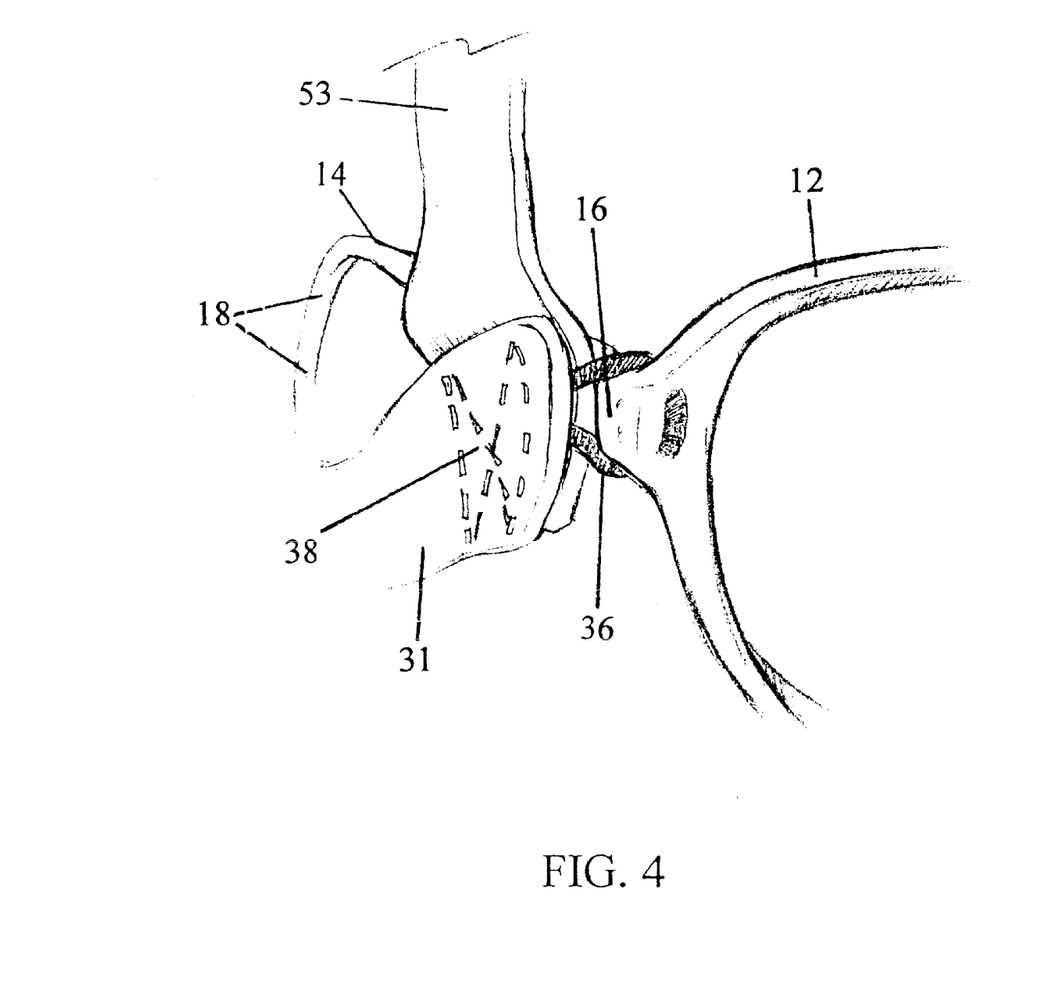
FIG. 4 is a perspective view of a portion of the strap assembly according to FIG. 3, showing the left front corner of the strap assembly attached to the eyeglasses.

Referring to FIGS. 2 and 4, the left lower strap portion is attached to the left corner of the eyeglass frame 12 at the left temple hinge 16 by means of a temple hinge loop 36. FIG. 4 shows the connection of the left front corner of the strap assembly 10 to the left temple hinge 16 of the eyeglasses 11. Referring to FIG. 2, the right lower portion is similarly attached to the right corner of the eyeglass frame 12 at the right temple hinge 15 by means of a temple hinge loop 26. For purposes of illustration, the right front corner of the assembly 10 is shown flipped back in FIG. 2. Each temple hinge loop 26, 36 is preferably attached to the corresponding strap portion by a loop sleeve 27 (see FIG. 2). The temple hinge loops ordinarily project slightly beyond the end of the strap. With the loop sleeve 27 in place, it is less likely that the temple hinge loop 26, which is preferably elasticized, will pull out and snap with repeated use. As indicated in FIG. 4, the loop sleeves are attached to the strap portion by stitching 38, adhesive, or any other suitable means. In use, the end of each eyeglass temple 13, 14 is inserted through each corresponding temple hinge loop 26, 36, and the hinge loop is slid up the eyeglass temple until the hinge loop lodges at approximately the hinge 15, 16 of the eyeglasses. In FIG. 4, the center of the hinge loop 36 is visible through the eyeglass frame 12, as if the frame is made of a translucent plastic material. Any conventional type of eyeglasses can be used with the present invention.

Referring again to FIG. 1, when worn in position as intended, each lower strap portion passes beneath the wearer's ear toward the back of the head, where it is joined to the other portion by means of the squeeze clasp 25, 35. Because the clasp is joined below the bulge of the skull above the neck and tightened securely but not uncomfortably, the lower strap section 20, 30 of the strap assembly 10 holds the eyeglasses in place and prevents them from being easily pulled off either from the front or up over the head. Young children find it quite difficult, and usually impossible, to remove this strap assembly from their own heads, or even, in the case of multiples, from each other's heads. In fact, the headgear assembly of the present invention is especially useful for keeping eyeglasses, with or without eyepatches, on twins, triplets or quadruplets. The parent or caregiver has greater flexibility once he or she is freed from the task of hovering over the child or children to assure that their eyeglasses are not removed. This strap assembly is especially useful on children from about nine months of age to about three or four years old. It is particularly difficult to keep glasses on the head of a baby (about nine to twelve months of age) or toddler (between one and about three years of age).

As shown in FIG. 2, the upper strap portion of the strap assembly 40 preferably consists of a pair of straps aligned crosswise over the top of the wearer's head, that is, in an "X" pattern, intersecting through a center buckle 41 at the top of the head. Referring to FIG. 1 and FIG. 2, the left-front-to-right-rear strap section 53 is attached by stitching 38 or any other suitable means to the left front side strap segment 31. The right-front-to-left-rear strap section 43 is similarly attached to the right front side strap segment 21. The left-front-to-right-rear upper strap section 53 runs from the left front corner of the assembly 10, at the point of attachment to the left front side strap 31, passing through the center buckle 41, to the right rear strap segment 24 of the assembly 10. Referring to FIG. 2 and FIG. 3, the bottom flap 58 of the left-front-to-right-rear upper strap section 53 loops around the right rear strap segment 24, doubles back on itself, and is fastened by means of a buckle 57 or other suitable means of attachment. The right-front-to-left-rear upper strap section 43 similarly runs from the right front corner of the assembly 10, at the point of attachment to the right front side strap 21, passing through the center buckle 41, to the left rear strap segment 34 of the assembly 10. The bottom flap 48 of the right-front-to-left-rear strap section 43 loops around the left rear strap segment 34, doubles back on itself, and is fastened by means of a buckle 47 or other suitable means of attachment.

Referring to FIGS. 2 and 3, a connecting loop 44 in two parts is attached to the right-front-to-left-rear strap section 43 immediately in front of the left rear buckle 47. The connecting loop 44 is sewn in two, or otherwise divided onto two portions or loops of unequal size. The larger posterior portion 45 passes snugly around the front-to-rear strap section 43 and the smaller anterior loop portion 46 projects in front of the strap section 43. A similar connecting loop 54, with posterior portion 55 and anterior loop portion 56, is attached to the left-front-to-right-rear upper strap section 53, as shown in FIG. 3, but not in FIG. 2. FIG. 3 shows the right side of a strap assembly 10, which is removably connected to a pair of eyeglasses. In use, the end of each eyeglass temple 13 or 14 is pushed through the anterior loop portion 46 or 56 of the bow connecting loop until the anterior loop portion is at the bow 17 or 18, respectively, of the eyeglasses.

Referring to FIGS. 1 and 3, when worn in position as intended, the right-front-to-left-rear strap 43 runs generally vertically from the eyeglass frame 12 at the right temple hinge 15 up over the wearer's head and angles towards the rear of the head. At the top of the wearer's head, it passes through the center buckle 41 and down the other side of the head, generally still toward the rear, where it connects to the left lower strap section 30 of the strap assembly. Referring to FIG. 1, the left-front-to-right-rear upper strap section 53 similarly runs generally vertically from the eyeglass frame 12 at the left temple hinge 16 up over the wearer's head and angles towards the rear of the head. At the top of the wearer's head, it passes through the center buckle 41 and down the other side of the head, generally still toward the rear, where it connects to the right lower strap section 20 of the strap assembly. As shown in FIG. 3, the connecting loop anterior portion 56 on the left-front-to-right-rear upper strap section 53 fits snugly over the bow 17 of the right eyeglass temple 13 and thus connects the upper strap portion of the strap assembly securely to the eyeglasses. Similarly, referring to FIGS. 1 and 2, the connecting loop anterior portion 46 on the right-front-to-left-rear upper strap section 43 will fit snugly over the bow 18 of the left eyeglass temple 14 and thus connect the upper portion of the strap assembly securely to the eyeglasses. The upper strap portion 40 of the strap assembly 10 thus prevents the eyeglasses from falling down over the wearer's face and also restrains the wearer from removing the eyeglasses by pulling them down.

When properly worn, the strap assembly 10 is thus connected securely to the eyeglasses 11 at four different positions, specifically, the left temple hinge 16, the right temple hinge 15, the left bow 18, and the right bow 17. Because the strap assembly 10 is connected at four corners of the eyeglasses (two hinges and two bows), it provides a more secure fit and stable restraint than can be achieved by a retainer attached only at the bows.

Figure 5:
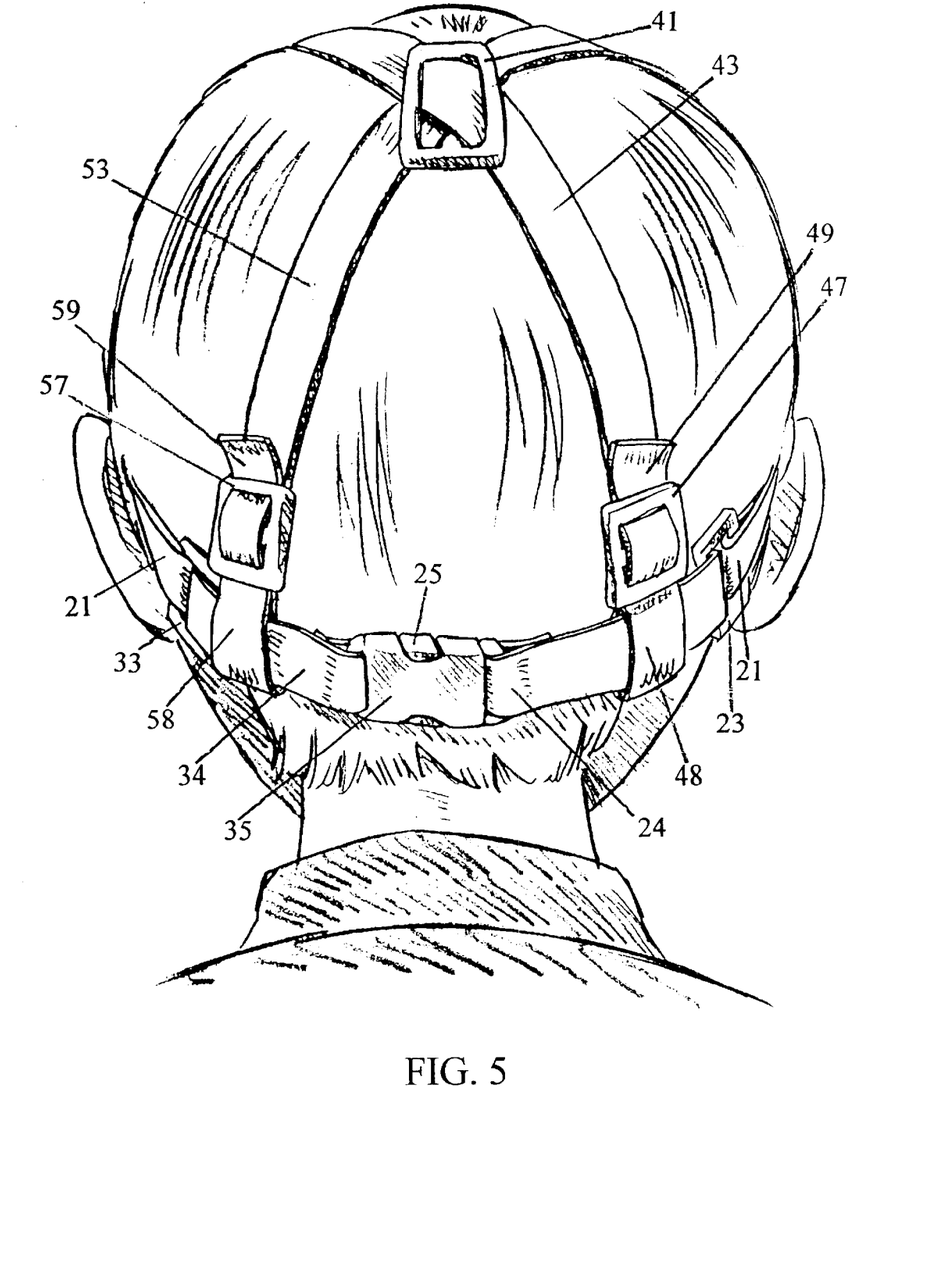
FIG. 5 is a perspective view of a strap assembly according to the present invention, shown in use.

Turning to FIG. 5, a strap assembly 10 is shown in use on a child's head. The center buckle lies on the crown of the wearer's head. The two upper strap sections 43, 53 both slide through the center buckle 41, one on top of the other. The center buckle 41 is preferably made of a smooth rubber or plastic material. As shown in FIG. 2, hook and loop strips 42 at the center buckle 41 keep the upper strap sections 43, 53 from sliding once the assembly 10 is in place on the wearer's head. The upper strap 43 or 53 on top has a strip of hook and loop affixed underneath it facing in a downward direction, and the upper strap section 43 or 53 which travels underneath the other upper strap has a corresponding strip of hook and loop 42 attached to it which is facing upward. Under the center buckle 41, the upper strap on top is thus removably affixed to the upper strap underneath. This hook and loop fastener prevents the upper straps from sliding around on the crown of the wearer's head during activities. It also provides cushioning, which is particularly desirable on a thin-haired, soft-headed baby or toddler.

Continuing with FIG. 5, the bottom flaps 48, 58 of the upper strap sections 43, 53 loop around the rear strap segments 24, 34, respectively, and double back on themselves. Each bottom flap 48, 58 is looped back on itself through a rear buckle 47, 57, leaving a rear tongue 49, 59 emerging from the upper end of each rear buckle 47, 57. The rear tongues 49, 59 can optionally be removably attached to the upper strap sections 43, 53 underneath by short hook and loop strips (not shown). The caregiver can independently adjust each upper strap section 43, 53, then, by pulling (to tighten) or pushing (to loosen) the appropriate tongue 49, 59. The upper strap sections 43, 53 can be pushed farther apart from each other by sliding the bottom flaps 48, 58 towards the wearer's ears. Likewise, the upper strap sections 43, 53 can be moved closer toward each other by sliding the bottom flaps 48, 58 toward the squeeze clasp 25, 35.

As described herein, the strap assembly 10 can also be adjusted by varying the position of the rear flaps 22, 32 of the front side strap segments 21, 31. Pulling one or both of the rear flaps 22, 32 tighter around the side buckles 23, 33, respectively, and then lightly pushing the rear flaps down on the hook and loop fastener 37 underneath tightens the strap assembly 10 to fit the wearer's head. The rear flaps 22, 32, which preferably fit loosely across the wearer's ear lobes, can be gradually loosened as the wearer grows. The rear flaps need not be tightened each time the strap assembly is placed on the wearer's head.

To use, after sliding the eyeglasses 11 into the strap assembly 10 as described herein, the caregiver places the eyeglasses on the wearer and then drapes the strap assembly over the wearer's head. The caregiver then pushes the male portion 25 of the clasp into the female portion 35 of the clasp approximately at the nape of the neck. The caregiver can easily remove the strap assembly 10 by squeezing the side of the male portion 25 of the clasp and extracting it from the female portion 35 of the clasp. The strap assembly can be stored with the eyeglasses 11 in place, e.g., at bedside while the child naps, and then quickly reapplied. If desired, the eyeglasses 11 can be removed from the strap assembly 10 for storage of the strap assembly.

The strap assembly may be made of any suitable material, but is preferably substantially constructed of a sturdy fabric that is comfortable and easily washable. The assembly is preferably made of durable, comfortable, washable, quick drying materials, and can easily be spot washed or laundered. The material is preferably not elastic in order to inhibit easy removal by the child or adult wearer, or by other children.

The wearer's hair can be draped over the straps of the assembly, if the caregiver or wearer desire to hide most of the assembly. The strap assembly is preferably brightly patterned and/or colored, though, so that it is visible and aesthetically pleasing. While the invention is of particular use with children, it is equally applicable to other wearers who may inappropriately remove and lose or damage their eyeglasses, such as mentally incompetent, autistic, or disabled persons, or to any others who need a means of securing their eyewear during strenuous physical activity.

Figure 6:
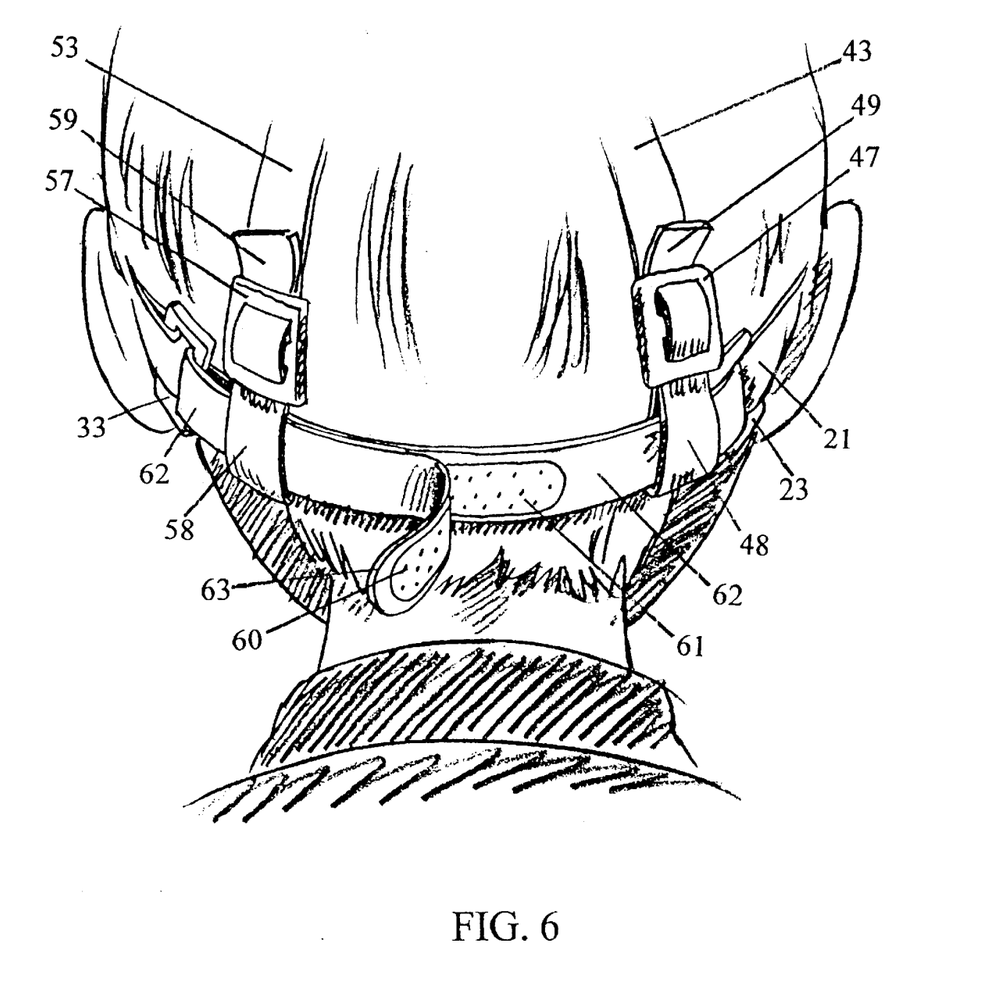
FIG. 6 is a perspective view of a portion of an alternate embodiment of a strap assembly according to the present invention, shown in use.

With reference to FIG. 6, a rear portion of an alternate embodiment of the strap assembly 10 is illustrated in place on a child's head. This embodiment employs complementary rear hook and loop strips 60, 61 instead of a squeeze-type clasp (25, 35). This embodiment of a strap assembly 10 has one rear strap segment 62 instead of two (24, 34). This rear strap segment 62 extends between the two side buckles 23, 33. In FIG. 6, the rear strap segment 62 is affixed to right side buckle 23 and extends across the back of the child's head to left side buckle 33. The rear strap segment 62 then passes through left side buckle 33 and through bottom flap 58. Two complementary strips of hook and loop material 60, 61 are affixed to rear strap segment 62. One strip 61 faces in an upward direction from the approximate middle of the rear strap segment 62 where it crosses the center of the back of the head. The other, complementary strip 60 faces in a downward direction from the end, or rear tongue 63, of the rear strap segment 62. Once the caregiver places the strap assembly on the wearer's head, he or she lightly presses the rear tongue 63 with its hook and loop strip 60 down over the corresponding strip of hook and loop 61. The strap assembly is thus easy to put on and take off.

Figure 7:
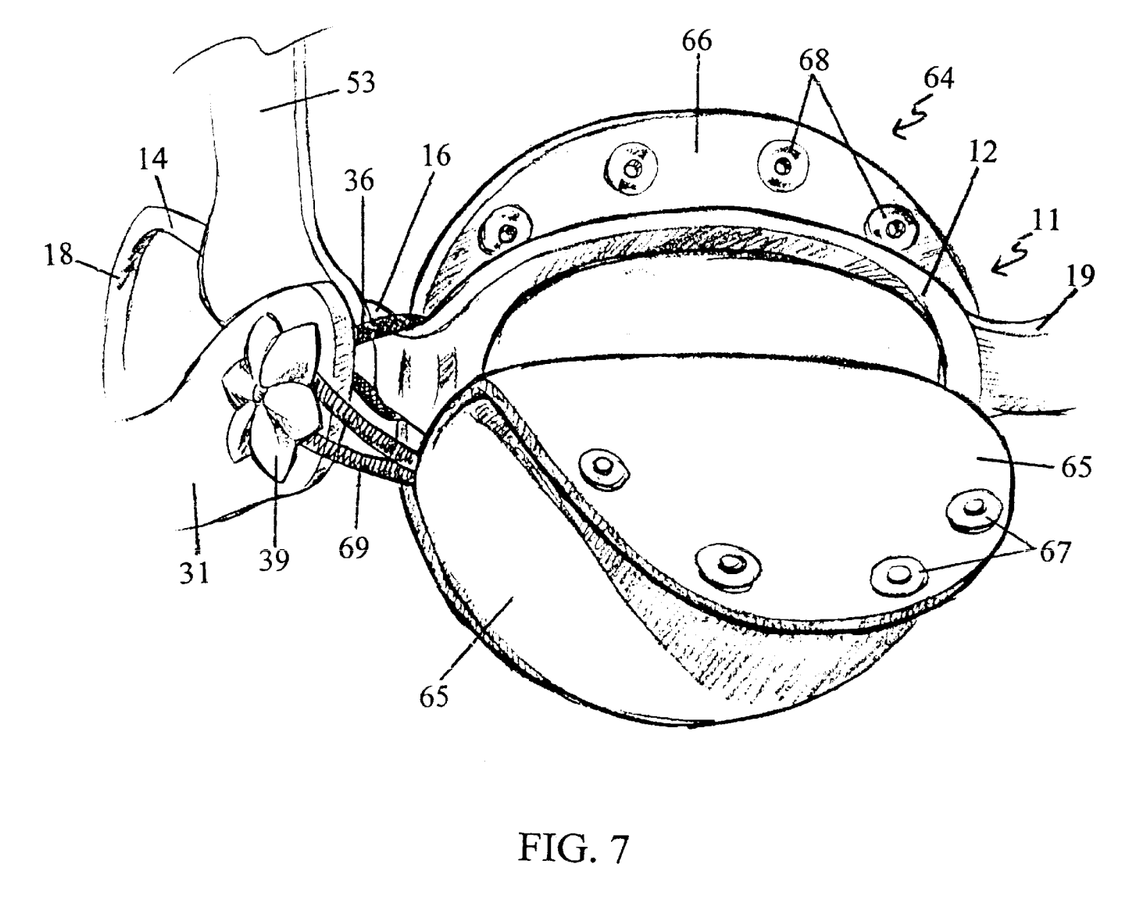
FIG. 7 is a perspective view of a portion of a strap assembly according to the present invention, showing a patch in place over a lense of the eyeglasses.

Referring to FIG. 7, the strap assembly optionally comprises a removable, reversible patch assembly 64. The patch assembly is comprised of a first patch portion 65 and a second patch portion 66. Either patch portion 65, 66 can face outward away from the eye or inward toward the eye of the wearer. The same patch assembly 64 can be attached to the strap assembly 10 so as to cover either the right eye or the left eye. The first patch portion and the second patch portion, which are substantially mirror images, are preferably sewn together at the bottom third or so. Complementary snap fasteners are affixed to the upper edge of the inside of each patch portion at corresponding locations. In FIG. 7, male snap members 67 are affixed to the inside face of the first patch portion 65, and complementary female snap portions 68 are affixed to the inside face of the second patch portion 66. The patch portions thus form a pocket for holding the bottom portion of a lense of a pair of eyeglasses 11. In use, the snap portions on each patch portion are then fastened to each other over the top of the eyeglass lense. The eyeglass bridge 19 on the inside and the eyeglass temple 14 on the opposite side fit through the openings left between the sewn lower third of the patch assembly 64 and the upper snapped one third of the patch assembly. An elasticized patch loop 69 is sewn at both ends to the patch assembly 64 at the opening through which the eyeglass temple will pass. To apply the patch assembly 64, the caregiver slides the patch assembly up over the desired lense, then squeezes the snaps closed. The caregiver then pulls the elasticized patch loop 69 over a decorative button 39 sewn to the outside front corner of the left or right front side strap segment 21, 31. A snap or other suitable type of fastener could be used instead of a button. The elasticized patch loop 69 holds the patch assembly 64 on the strap assembly 10. This does not interfere with the front temple hinge loop 26, 36, which is used to hold the strap assembly 10 to the glasses at the temple hinges 15, 16. If desired, the patch assembly 64 can be removed, flipped, and reapplied over the other eyeglass lense. The patch assembly is preferably made of a washable, nonabrasive, decorative fabric.

In short, the strap assembly 10 includes:
a. a flexible lower strap portion comprised of at least two lower strap sections 20, 30, each lower strap section having a front end 28 and a rear end 29;
b. a means 50 of detachably attaching the rear ends of the two lower strap sections to one another;
c. a means 26 of attaching the front ends of the two lower strap sections to opposite temples of the eyewear;
d. a flexible upper strap portion 40 comprised of at least two upper strap sections 43, 53, each upper strap section having a front end 51 and a rear end 48, 58, the front and rear ends 51, 48, 58 of each upper strap section being affixed to a lower strap section, the front and rear ends of each upper strap section being affixed to a different lower strap section; and
e. a means of adjusting 23, 33, 41, 47, 57 the strap assembly 10 to fit the head of the eyewear wearer. Preferably: The rear ends of the upper strap sections comprise a means of removable attachment to the bows 17, 18 of the eyewear. The lower strap sections 21, 31 are substantially mirror images of each other, and the upper strap sections 43, 53 are substantially mirror images of each other. The means of removable attachment to the bows 17, 18 is a bow connecting loop 54. The eyewear is a pair of eyeglasses, and opposite strap portions are attachable to corresponding opposite temples and bows of the eyeglasses. The bow connecting loop comprises an anterior loop portion 55 slidably attached to the upper strap section, and a posterior loop portion 56 adapted for sliding over the eyeglass bow.

From the foregoing it can be realized that the described device of the present invention. It is to be understood that any dimensions given herein are illustrative, and are not meant to be limiting.

While preferred embodiments of the invention have been described using specific terms, this description is for illustrative purposes only. It will be apparent to those of ordinary skill in the art that various modifications, substitutions, omissions, and changes may be made without departing from the spirit or scope of the invention, and that such are intended to be within the scope of the present invention as defined by the following claims. It is intended that the doctrine of equivalents be relied upon to determine the fair scope of these claims in connection with any other person's product which fall outside the literal wording of these claims, but which in reality do not materially depart from this invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

BRIEF LIST OF REFERENCE NUMBERS USED IN THE DRAWINGS (For Information Only)

10 eyewear retainer strap assembly
11 eyeglasses 12 eyeglasses frame
13 eyeglasses right temple
14 eyeglasses left temple
15 eyeglasses right temple hinge
16 eyeglasses left temple hinge
17 eyeglasses right bow
18 eyeglasses left bow
19 eyeglass bridge
20 right lower strap section
21 right front side strap segment
22 rear flap of right front side strap segment
23 right side buckle
24 right rear lower strap segment
25 right rear male clasp portion
26 right front temple hinge loop
27 right front temple hinge loop sleeve
28 front ends of lower strap sections
29 rear ends of lower strap sections
30 left lower strap section
31 left front side strap segment
32 rear flap of left front side strap segment
33 left side buckle
34 left rear lower strap segment
35 left rear female clasp portion
36 left front temple hinge loop
37 left hook and loop fasteners
38 left front stitching
39 button
40 upper strap portion
41 upper center buckle
42 center hook and loop fastener
43 right-front-to-left-rear strap section of upper strap portion
44 left bow connecting loop
45 posterior portion of left bow connecting loop
46 anterior loop portion of left bow connecting loop
47 left rear buckle of upper strap portion
48 bottom flap of right-front-to-left-rear strap of upper strap portion
49 right strap tongue
50 means of attaching rear ends of lower strap sections
51 front ends of upper strap sections
53 left-front-to-right-rear strap section of upper strap portion
54 right temple bow connecting loop
55 posterior portion of right temple bow connecting loop
56 anterior loop portion of right temple bow connecting loop
57 right rear buckle of upper strap portion
58 bottom flap of left-front-to-right-rear strap of upper strap portion
59 left strap tongue
60 rear strip of hook and loop
61 corresponding strip of hook and loop
62 rear strap segment
63 rear tongue
64 patch assembly
65 first patch portion
66 second patch portion
67 male snap member
68 female snap member
69 elasticized patch loop

What is claimed is:

1. A child-proof strap assembly for retaining eyewear on a wearer's head, the strap assembly comprising:

a. a flexible lower strap portion comprised of at least two lower strap sections, each lower strap section having a front end and a rear end;

b. a means of detachably attaching the rear ends of the two lower strap sections to one another;

c. a means of attaching the front ends of the two lower strap sections to opposite temples of the eyewear;

d. a flexible upper strap portion comprised of at least two upper strap sections, each upper strap section having a front end and a rear end, the front and rear ends of each upper strap section being affixed to a lower strap section, the front and rear ends of each upper strap section being affixed to a different lower strap section; and e. a means of adjusting the strap assembly to fit the head of the eyewear wearer.

2. An assembly according to claim 1, wherein the rear ends of the upper strap sections comprise a means of removable attachment to the bows of the eyewear.

3. An assembly according to claim 2, wherein the lower strap sections are substantially mirror images of each other.

4. An assembly according to claim 3, wherein the means of removable attachment to the bows is a bow connecting loop.

5. An assembly according to claim 4, wherein the upper strap sections are substantially mirror images of each other.

6. An assembly according to claim 5, wherein the eyewear is a pair of eyeglasses, and opposite strap portions are attachable to corresponding opposite temples and bows of the eyeglasses.

7. An assembly according to claim 5, wherein the bow connecting loop comprises an anterior loop portion slidably attached to the upper strap section, and a posterior loop portion adapted for sliding over the eyeglass bow.

8. An assembly according to claim 1, wherein the means of detachably attaching the rear ends of the two lower strap sections to one another is a clasp.

9. An assembly according to claim 2, wherein the means of detachably attaching the rear ends of the two lower strap sections to one another is lock and loop material.

10. An assembly according to claim 1, the upper strap sections being crossed over one another at their centerpoints.

11. An assembly according to claim 5, the upper strap sections being detachably affixable to one another at their respective centerpoints.

12. An assembly according to claim 5, wherein the means of attaching the front ends of the two lower strap sections to opposite temples of the eyewear is an elasticized loop.

13. An assembly according to claim 12, wherein the elasticized loop is attached to a sleeve, the sleeve being attached to the lower strap section.

14. An assembly according to claim 1, wherein the means of adjusting the strap assembly to fit the head of the wearer comprises a buckle and lock and loop strips affixed to the upper strap sections.

15. An assembly according to claim 1, wherein the lower strap sections are each comprised of two lower strap segments, and the means of adjusting the strap assembly to fit the head of the wearer comprises at least two buckles and lock and loop strips affixed to the lower strap sections.

16. An assembly according to claim 6, wherein the strap assembly is removably attachable to the eyeglasses at four points for stability and security.

17. An assembly according to claim 16, wherein the four points are the eyeglass temple hinges and the eyeglass ear bows.

* * * * *